United States Patent [19]

Decavel et al.

[11] 4,253,113
[45] Feb. 24, 1981

[54] METHOD AND APPARATUS FOR DETECTING SURFACE DEFECTS ON A BAND TRAVELLING AT HIGH SPEED

[75] Inventors: Bernard Decavel, Malo les Bains Dunkerque; René Dubourg, Bourbourg; Jacques Questier, Watten; Jacques Pinard, Saint-Germain en Laye, all of France

[73] Assignee: Union Siderurgique du Nord et de l'Est de la France (USINOR), Paris, France

[21] Appl. No.: 941,738

[22] Filed: Sep. 12, 1978

[30] Foreign Application Priority Data

Sep. 12, 1977 [FR] France ............... 77 27501

[51] Int. Cl.³ .............................. H04N 7/18
[52] U.S. Cl. .................... 358/106; 250/563; 356/430
[58] Field of Search .......... 358/101, 106, 93, 107; 250/563, 572; 356/429, 430, 431, 238

[56] References Cited

U.S. PATENT DOCUMENTS

| | | | |
|---|---|---|---|
| 3,111,555 | 11/1963 | Dykeman et al. | 358/106 |
| 3,158,748 | 11/1964 | Laycak et al. | 358/106 |
| 3,280,692 | 10/1966 | Milnes et al. | 358/106 |
| 3,389,789 | 6/1968 | Watson et al. | 250/563 |
| 3,419,677 | 12/1968 | Fiori | 358/106 |
| 3,835,247 | 9/1974 | Soames | 358/93 |
| 3,868,478 | 2/1975 | Zeenkov | 358/93 |
| 3,988,530 | 10/1976 | Ikegami et al. | 356/430 |
| 4,110,048 | 8/1978 | Akutsu et al. | 250/563 |

FOREIGN PATENT DOCUMENTS 682892 3/1964 Canada ................... 358/106

*Primary Examiner*—Richard Murray
*Assistant Examiner*—Joseph A. Orsino, Jr.
*Attorney, Agent, or Firm*—Burns, Doane, Swecker & Mathis

[57] ABSTRACT

This apparatus comprises a device for illuminating in a permanent manner a zone in which the band travels, a television camera having a high luminous sensitivity and a low remanence controlled for exposure during constant periods of time which are short relative to the speed of travel of the band with a frequency of recurrence which is substantially equal to the speed of the band divided by the length of said zone in the direction of travel of the band. In this way, said successive images detected constitute a substantially continuous representation of the band. An electronic circuit is provided for analysing the images received by the camera.

4 Claims, 4 Drawing Figures

FIG_1
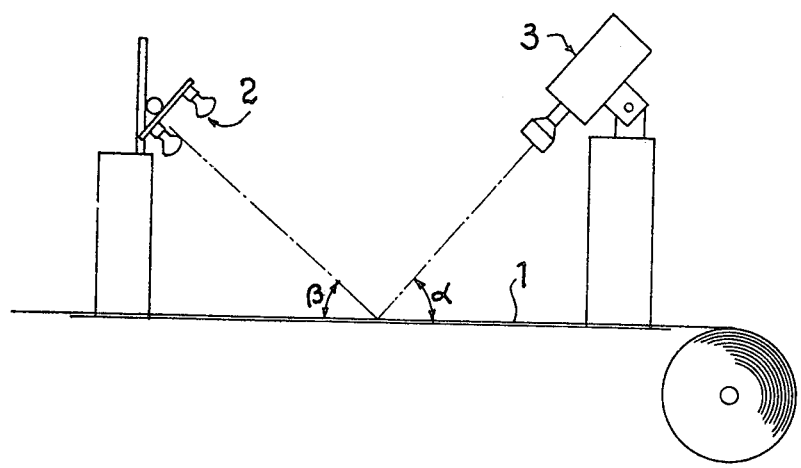
FIG_3
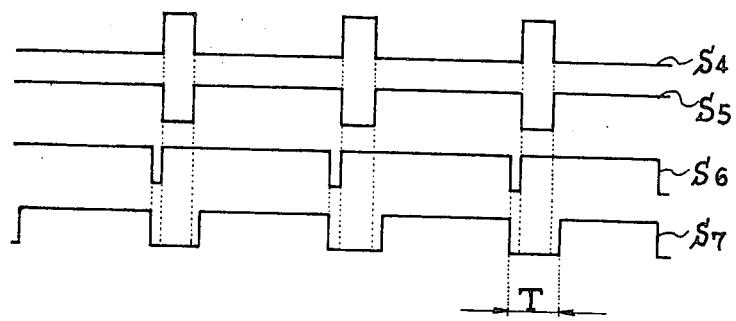

METHOD AND APPARATUS FOR DETECTING SURFACE DEFECTS ON A BAND TRAVELLING AT HIGH SPEED

The present invention relates to a method and apparatus for detecting defects on a band travelling at high speed and more particularly on a hot rolled band.

There is known a method comprising permanently illuminating a zone in which the band travels, sequentially scanning said zone by means of a photosensitive device so as to form upon each scanning an image representing substantially the part of the band which is located in said zone with a frequency for repetition related to the speed of the band whereby said image constitute a substantially continuous representation of the band, analyzing said signal constituting said images by comprising it with at least one predetermined threshold voltage so as to detect said surface defects.

However, this known method employs either a rotary mirror or a camera mounted to be rotatable so that the image appears fixed relative to the objective of the camera, which requires complicated circuits and circuits which are therefore unreliable, to ensure the movement of rotation of the camera or of the mirror in synchronism with the movement of the band.

An object of the invention is to overcome this drawback and to provide a method and device which permit detecting by means of a photosensitive device defects on the whole of the length of a band travelling at high speed and which does not require the use of moving parts.

According to the invention there is provided a method comprising permanently illuminating a zone in which the band travels, sequentially scanning said zone by means of a photosensitive device so as to form upon each an image representing substantially the part of the band which is located in said zone with a frequency for repetition related to the speed of the band whereby said images constitute a substantially continuous representation of the band, and analyzing said signal constituting said images by comparing it with at least one predetermined threshold voltage so as to detect said surface defects, wherein said zone is placed directly in the area of operation of said photosensitive device, their relative position being fixed, and said zone is scanned during constant periods of time which are very short relative to the speed of travel of the band with a frequency of repetition substantially equal to the speed of the band divided by the length of said zone in the direction of travel of the band.

Another object of the invention is to provide an apparatus for carrying out the method defined hereinbefore comprising a device for illuminating said zone, a television camera having a high luminous sensitivity and low remanence and a very short exposure time, and an electronic circuit for comparing the video signal of the camera with said threshold level.

Further features and advantages of the invention will be apparent from the ensuing description with reference to the accompanying drawings given solely by way of example and in which:

FIG. 1 is a diagrammatic elevational view of an apparatus according to the invention;

FIG. 3 is the diagram showing the synthesis of the signal for illuminating the parasitic spikes of the video signal at the start and end of the line.

Figure 2A:
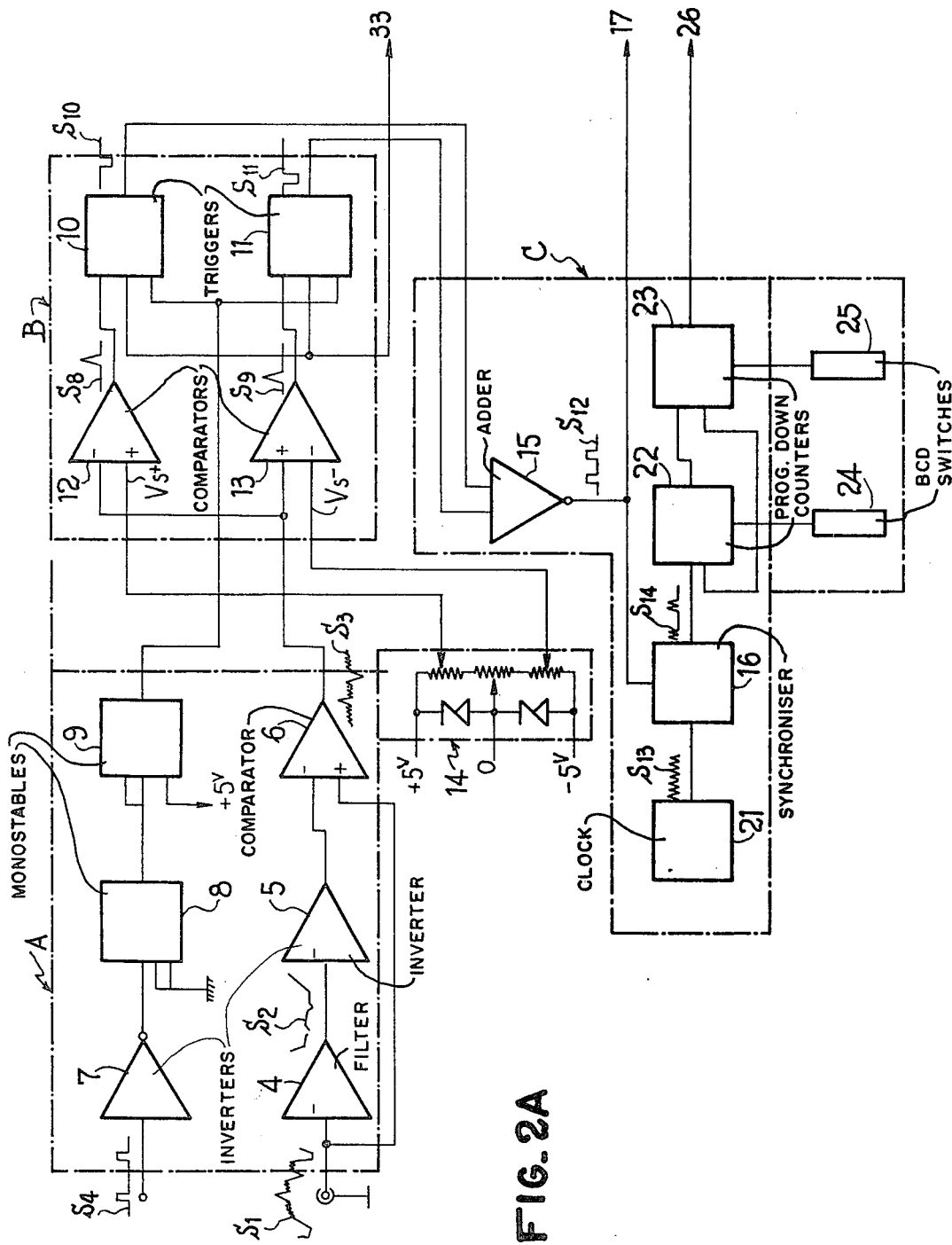
FIGS. 2A and 2B are diagrams of the electronic circuit of the apparatus according to the invention.

With reference to FIG. 1, there is shown an apparatus according to the invention disposed above a band 1 for example a hot rolled band which travels at high speed of the order of 20 meters per second.

This apparatus comprises an illuminating unit 2 which in respect of a band having a width of about 1 meter may comprise, for example, two rows of three spot-lights of 150 watts each and spaced apart 30 centimeters so as to ensure an illumination which is such that in the region of the photosensitive device, there is received, in the absence of a defect, an electric signal of constant amplitude throughout the image.

Preferably, the mean angle of incidence $\beta$ of the illuminating unit relative to the band is between about 30° and 40°.

The apparatus also comprises a photosensitive detecting device 3 having a high luminous sensitivity and low remanence disposed also above the band 1 at a given distance from the illuminating unit 2. Preferably, the photosensitive device 3 is a television camera disposed at an angle of incidence $\alpha$ of for example about 45° with respect to the band so as to obtain an optimum definition of the defects and covering, in the case of a band having a width of 1 meter, an area or field of 1 meter square in the illuminated zone. A television camera which is particularly suitable for carrying out the method of the invention is that commercially available under the name SOFRETEC CF 261 equipped with an ISOCON tube (English electric valve) and which has a very high sensitivity (of the order of $10^{-4}$ lux), a very low remanence, a good dynamic, an adjustable exposure time of 20 microseconds to 20 milliseconds, and a duration of reading of an image of 20 milliseconds. Further, this camera is provided with a remote controlled objective which enables the focusing and adjustment of the diaphragm and an adjustment of the magnification to be carried out.

By way of example, by adopting an exposure time of 80 $\mu$s, which is a suitable value bearing in mind the conditions of illumination, it is possible to observe bands with a speed of travel which may reach 20 meters per second. However, in the case of the observation of hot rolled bands, to which the invention is more particularly applicable, the speed of travel of the band is more generally of the order of 10 to 15 meters per second. Thus, for example, with a band travelling at 17 meters per second and with a field or area of 1 square meter the frequency of recurrence will be 17 pictures per second so as to reconstitute by successive images the whole of the band. It is found that the time between two successive pictures is amply sufficient to permit the exposure (80 $\mu$s), then the reading (20 ms) of the image. With such a speed of travel of 17 meters per second and such an exposure time of 80 $\mu$s, a surface defect of 10×10 mm moves 1.36 millimeters during the exposure time, which results in an uncertainty of 13.6 mm² which is quite acceptable with respect to the area of 100 mm² of the defect.

Figure 2B:
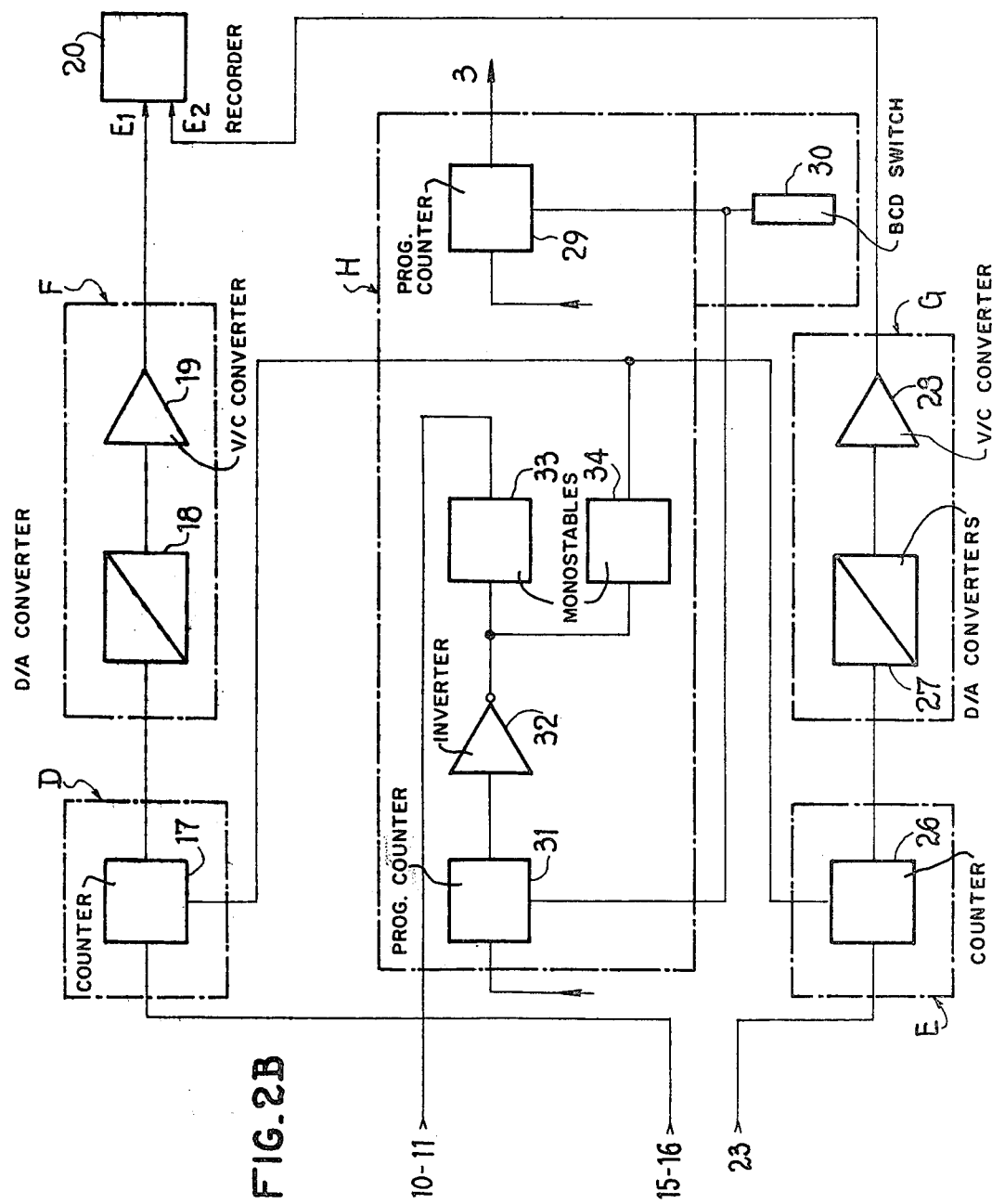

With reference now to FIGS. 2A and 2B which show the electronic circuit for processing signals coming from the television camera 3, this circuit comprises a shaping stage A, a trigger stage B, an area weighting stage C, a stage D for counting the number of defects on an image, a stage E for calculating the area of the defects as a pourcentage of the area of the image, an output stage F of the stage D, an output stage G of the stage E, a resetting and blocking stage H for the trigger stage B.

The video output signal $S_1$ of the television camera 3 is applied to a low pass filter 4 whose attenuation is 12 dB/octave and in which the signal $S_1$ is filtered and inverted. The resulting signal $S_2$ is applied to the input of an inverter 5 whose output signal is applied, with the signal $S_1$, to the input of a comparator 6 which delivers a signal $S_3$ which discloses the defects relative to the reference of 0 volts. However, this signal $S_3$ has a serious drawback: spikes are produced by the leading and trailing edges at the start of an and at the end of the line. With such a signal, defects whose amplitude exceeds these spikes would be necessary to ensure correct triggerings. To overcome this drawback, the trigger stage B is blocked during the time T of passage of one line to the other. This blocking is ensured by a circuit comprising an inverter 7 to which the line synchronizing signal $S_4$ (FIG. 3) of the camera 3 is applied, and a first monostable circuit 8 triggered on the trailing edge of the inverted synchronization signal $S_5$. The calibrated output pulse of this first monostable circuit 8 is so regulated that the trailing edge of this pulse appears before the trailing edge of the following synchronization pulse, but as close as possible to the latter. The signal obtained $S_6$ is applied to a second monostable circuit 9 which is triggered in such manner as to obtain the required signal $S_7$ which serves to block the trigger circuits 10 and 11 of the stage B during the time T. Consequently, the parasitic pulses at the end of and beginning of the line are no longer a hinderance whatever be their magnitude.

The trigger stage B comprises also two comparators 12 and 13 each receiving the shaped video signal $S_3$. Moreover, the comparator 12 receives a threshold voltage $V_s^+$ corresponding to a maximum gray level, and the comparator 13 a voltage $V_s^-$ corresponding to a minimum gray level. These voltages $V_s^+$ and $V_s^-$ are delivered by a conventional circuit 14 comprising Zener diodes and a resistance dividing bridge which permits discriminating the "black" defects from the "white" defects. The output signals $S_8$ and $S_9$ of the amplifiers 12 and 13 are applied to the trigger circuits 10 and 11 which each comprise a NAND gate having three inputs which permits the blocking thereof during the time T and also during the non utilized frame owing to the circuit H will be described in more detail hereinafter, so as to suppress the remanence effects. The circuits 10 and 11 furnish the shaped signals to a level TTL 0–5B, the width of the signals depending on the width of the defect on the considered line.

The output signals $S_{10}$ and $S_{11}$ of the circuits 10 and 11 are added in an adder 15 of the weighting stage C. The output signal $S_{12}$ of the adder 15 is applied, on one hand, to the stage D, and, on the other hand, to a pulse synchronizer circuit 16.

The stage D comprises a counter 17 having four counting decades which is reset to 0 at the end of each analysis of the image by the circuit H. The output of the counter 17 is applied to the input of a digital-analog converter 18 having sixteen bits, the output of which is applied through a voltage-current converter 19, to the first input $E_1$ of a recorder 20 having three channels. The channel acted upon through the input $E_1$ therefore records an analog signal whose amplitude is proportional to the number of defects detected in each successive image of the band.

The video signal in the digital form $S_{12}$ is moreover mixed in the pulse synchronizer circuit 16 with a clock signal $S_{13}$ produced by a clock 21, for example a signal of 8 MHz, so as to obtain an output signal $S_{14}$. The circuit 16 takes into account an 8 MHz pulse of the signal $S_{13}$ which appears during the rise of the leading edge $S_{12}$ but does not take into account a 8 MHz pulse which appears during the decay of the trailing edge. Moreover, a resolution of 5 millimeters of the camera for a viewing field of 1 meter was assumed in one embodiment. Bearing in mind that the utilizable length of the line is 50 µs, the smallest defect therefore produces $50 \times 5/1000 = 250$ s, representing a frequency of 4 MHz. There will therefore be obtained two surface weighting pulses for the smallest defects taken into account.

Moreover, the number of surface defects may be very high (in the case for example of smut or gravel) or very low (one small defect). If there has been chosen a scale on the recorder which permits measuring a large area the data received will be very small if not illegible in the case of isolated small defects. In order to overcome this drawback, two decades of programmable down-counters 22 and 23 were used; the programming is achieved by two switches having a binary coded decimal logic output BCD 24 and 25 which permit a display of 1 to 99. The output of the down-counter 23 is applied to a counter 26 having three decades. The output stage G comprises a digital analog converter 27 having 12 bits and a voltage-current converter 28. This stage applies the output of the counter 26 to the input $E_2$ of the second channel of the recorder 20, the third channel of which is formed by a time reference. The recorder thus records a percentage of defective area per meter of sheet metal scanned. There was chosen for the recorder 20 a scale corresponding to 1,000 pulses of 8 MHz at the output of the circuits 22, 23. Thus, if 1% is displayed, a complete deflection of the recorder for 1,000 surface pulses of the signal $S_{14}$. If 10% is displayed, there will be had a complete deflection of the recorder for 10,000 surface pulses of the signal $S_{14}$. This is of great interest since it is thus possible to display a limit percentage of defective surface (as a function of a required sheet quality for example).

Thus, with regard to the recording, all the pulses located below this limit would correspond to acceptable defects and all those above this limit would correspond to portions of sheet to be rejected.

The stage H comprises a programmable counter 29 to which there is applied a synchronization signal coming from the fixed frequency electronic shutter. This programmable counter 29 counts down and the programming of the division is ensured by a switch 30 having a binary code decimal output which permits controlling the number of frames employed as a function of the speed of the band, that is to say the frequency of recurrence of operation of the camera. By way of a modification, in order to avoid any overlapping between two successive images, there may be employed an electric circuit controlling the triggering of the scanning as a function of the instantaneous speed of the band, and also of the width of the band since the depth of the field employed must vary as a function of this width.

The switch 30 also controls the programming of another programmable counter 31 to the input of which there is applied the frame synchronization signal. The output of this counter 31, after inversion by an inverter 32, is applied to two monostable circuits 33 and 34. The monostable circuit 33 which is regulated so as to have an output pulse which is slightly higher than 20 ms serve to deblock the trigger circuits 10, 11 during the frame employed. The latter are therefore blocked during the non utilized frame, namely between the end of the scanning of an image and the start of the scanning of the following image, which permits overcoming problems of remanence. The second monostable circuit 34 resets the counters 17 and 26 upon the appearance of the frame synchronization pulse.

By way of example, the following components may be employed for the circuits shown in FIGS. 2A and 2B:

| | | |
|---|---|---|
| Low pass filter | 4 | SN 72709 |
| Inverter | 5 | SN 72709 |
| Comparator | 6 | SN 72702 |
| Inverter | 7 | SN 7400 |
| Monostable circuits | 8, 9 | SN 74121 |
| Trigger circuits | 10, 11 | SN 7413 |
| Amplifiers | 12, 13 | SN 72702 |
| Adder | 15 | SN 7400 |
| Synchronizer circuit | 16 | SN 74120 |
| Counters | 17, 26 | SN 7490 |
| Clock | 21 | SN 7413 |
| Count-down-counters | 22, 23 | SN 74190 |
| Counters | 29, 31 | SN 74190 |
| Inverter | 32 | SN 7400 |
| Monostable circuits | 33, 34 | SN 74121 |
| Digital-analog converters | 18, 27 | CY 2735 |
| Voltage-current converters | 19, 28 | SN 72709 |
| Recorder | 20 | Siemens ink jet recorder |

Tests carried out with the apparatus described hereinbefore on hot rolled bands have revealed that it permits detecting all visible surface defects having a minimum size of about 5 mm, for example steel mill defects such as scales, and rolling defects such as gravel and inprints or grooves.

It must be understood that the invention is not intended to be limited to the detection of defects of hot rolled bands but is also applicable to the detection of defects on cold rolled bands or on any type of band having a uniform surface liable to include defects.

The circuit of the apparatus according to the invention has the advantage of permitting the determination of the number of defects in each given section of length of the band and the total area of the defects in each section as a pourcentage of the total area of this section. This data permits thereafter classifying the wound bands inspected into different categories in accordance with predetermined quality criteria.

Having now described our invention what we claim as new and desire to secure by Letters Patent is:

1. An apparatus for detecting surface defects on a continuous band travelling at high speed, comprising a device for illuminating a zone in which the band travels; a television camera having for each frame a constant exposure time so related to the speed of travel of the band as to record on the camera television tube a substantially instantaneous image of the portion of the band which is within said zone during the exposure time; exposure frequency control means for sequentially recording images on said tube with a frequency of repetition substantially equal to the speed of the band divided by the length of said zone in the direction of travel of the band whereby the successive recorded images constitute a substantially continuous representation of the band, said camera comprising means for scanning at a constant speed each image recorded on said tube and for producing a video output signal representative of said image; and an electronic circuit for comparing said video output signal with two opposite threshold voltages corresponding respectively to a minimum gray level and a maximum gray level, said electronic circuit comprising a shaping stage, a triggering stage and a circuit generating said two opposite threshold voltages, said shaping stage comprising a shaping circuit for shaping said video output signal and a blocking circuit receiving a line synchronizing signal from said camera and producing a blocking signal for blocking said triggering stage between the end of the scanning of a line and the beginning of the scanning of a following line of the camera, said triggering stage comprising two comparators for discriminating shaped defect signals produced by said shaping circuit relative to said opposite threshold voltages respectively and two gating circuits receiving said discriminated shaped defect signals respectively from said comparators and producing pulse defect signals, said two gating circuits receiving also said blocking signal from said blocking circuit and another blocking signal from said exposure frequency control means, so as to block said gating circuits between the end of the scanning of an image and the start of the scanning of the following image.

2. An apparatus as claimed in claim 1, wherein said electronic circuit comprises an adder for adding the pulse defect signals issued by said gating circuits and a first counter connected to the output of said adder and to the exposure frequency control means for counting the number of defects detected in each image.

3. An apparatus as claimed in claim 2, wherein the electronic circuit comprises a surface weighting stage, a second counter, first and second conversion output stages and a recorder, said surface weighting stage including a clock producing a clock signal, a pulse synchronizer circuit for mixing the clock signal with the output signal from said adder, programmable downcounter means connected between the output of the pulse synchronizer circuit and the input of the second counter, said first and second conversion output stages being connected between the outputs of said first and second counters respectively and two inputs of said recorder, said recorder receiving a time reference at a third input whereby said recorder records a percentage of defective area per length of scanned band.

4. An apparatus as claimed in claim 3, wherein the electronic circuit comprises a stage for resetting each counter to zero after the analysis of an image.

* * * * *